United States Patent [19]
Marrelli et al.

[11] Patent Number: 5,386,719
[45] Date of Patent: Feb. 7, 1995

[54] DEBRIS REDUCING TEST CELL FOR THREE PHASE METERS

[75] Inventors: John D. Marrelli, Houston; Joseph D. Stafford, Bellaire, both of Tex.

[73] Assignee: Texaco Inc., White Plains, N.Y.

[21] Appl. No.: 226,195

[22] Filed: Apr. 11, 1994

[51] Int. Cl.⁶ .............................................. G01N 22/00
[52] U.S. Cl. .................................... 73/61.44; 324/640
[58] Field of Search .............. 73/61.43, 61.44, 861.04; 324/640, 639

[56] References Cited

U.S. PATENT DOCUMENTS 5,140,271  8/1992  Marrelli ............................. 73/61.63
5,157,339  10/1992  Scott et al. ........................ 73/61.43

*Primary Examiner*—Herbert Goldstein
*Attorney, Agent, or Firm*—James L. Bailey; Kenneth R. Priem; Russell J. Egan

[57] ABSTRACT

In a three phase fluid stream microwave monitor, an improved test cell having a fluid stream flowing through it with spaced, aligned first and second antenna located within the test cell to receive microwave energy, irradiate the fluid stream, and receive the microwave energy which has passed through the fluid stream. The test cell has a rotatable cage mounted to form a cylinder enclosing the antennas for reducing an amount of debris in a portion of the petroleum stream flowing therebetween. The cage includes vanes which cause it to rotate, under the influence of the flowing stream to thereby be self-cleaning. The cage also carries a block which lies between the antenna and perpendicular to the axis thereof. Rotation of the cage causes rotation of this block to modulate the microwave transmission in a manner indicative of the fluid velocity.

9 Claims, 2 Drawing Sheets

DEBRIS REDUCING TEST CELL FOR THREE PHASE METERS

BACKGROUND OF THE INVENTION

1. The Field of the Invention

The present invention relates to a method and apparatus to provide three phase metering at substantially all flow rates and conditions and in particular, to a means and method to prevent entry of fluid borne debris to the test cell and adversely affect the operation thereof.

CROSS REFERENCE TO RELATED PATENTS

The present invention represents an improvement over my earlier invention described in U.S. Pat. No. 5,140,271, issued Aug. 18, 1992, the disclosure of which is incorporated herein by reference.

2. The Prior Art

There is a continuing need for metering of three phase fluids, such as petroleum fluids. This need has been addressed by many inventors. but their inventions all face the same problem in the wide fluctuations in component mixtures which can occur in fractions of a second making the exact timing of measurements critical if errors in the Net Oil (fraction of oil * Oil flow rate) are to be minimized.

The present invention is intended for use in combination with a known microwave three phase fluid measurement method and apparatus in which the oil, water, and gas ratio is combined with a mechanical device whose rotary action modulates the microwave signal with a frequency component related to the flow rate.

Several rotary devices of the present design can be placed in series on a single interrupted waveguide, each rotary device having a specific signature effect on the modulated microwave signal. If these devices are placed perpendicularly to a three phase fluid stream in a pipeline, they can average fluid fraction over different regions of the pipe and also provide specific local flow rates of that region. The value of this option is that separated fluid flow, such as annular flow, could be detected and slip velocities could be estimated or responded to in some manner.

SUMMARY OF THE INVENTION

A test cell for a three phase fluid monitor, according to the present invention, has a petroleum stream flowing through it. A microwave energy source provides microwave energy to a first antenna within the test cell, so as to irradiate the three phase stream passing through the test cell with microwave energy. A second antenna, also located within the test cell, receives the microwave energy that has passed through the fluid stream and sends it to detector means outside the cell. The detector means provides a signal the intensity of which corresponds to the received microwave energy. Display means show the watercut of the three phase stream in accordance with the intensity and the phase differences between the transmitted and the received microwave energy. The test cell also includes means for reducing the amount of debris in the portion of the fluid stream flowing between both antenna.

BRIEF DESCRIPTION OF THE DRAWINGS

The present invention will now be described, by way of example, with reference to the accompanying drawings in which.

DETAILED DESCRIPTION OF THE PREFERRED EMBODIMENT

Figure 1:
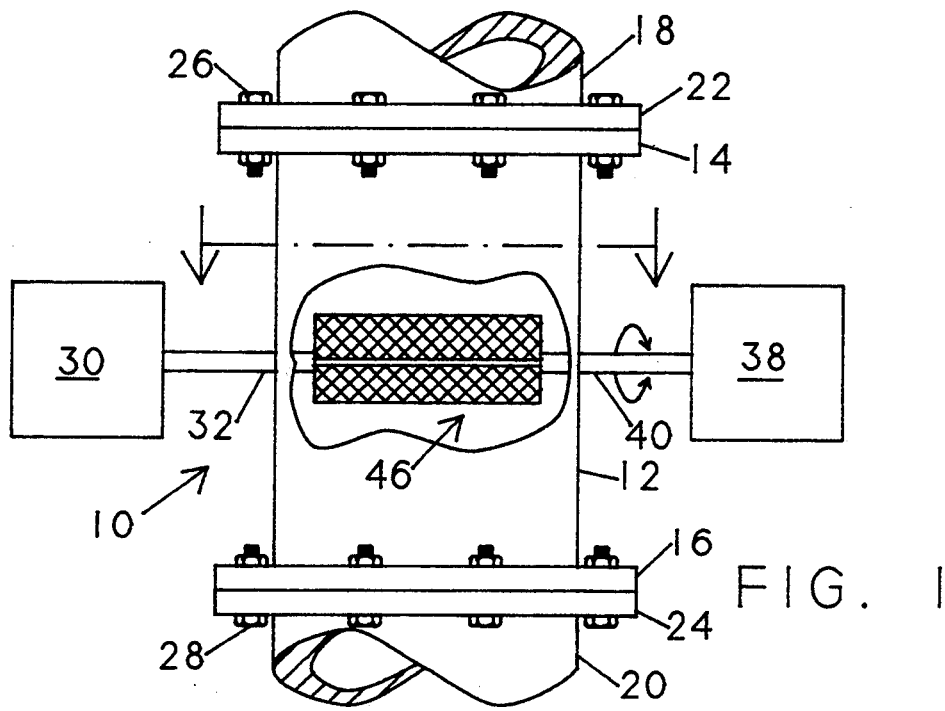
FIG. 1 is a side elevation, partially in section and partially schematic, of a test cell in accordance with the present invention.
Figure 3:
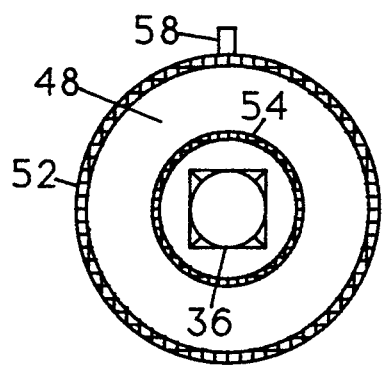
FIG. 3 is a further transverse section taken along line 3—3 in FIG. 2, on a still larger scale.

Referring now to FIG. 1, the subject test cell 10 is shown as a pipe segment 12 having flanges 14, 16 on opposite ends thereof for mounting the cell between flanges 18, 20 of pipes 22, 24 of a fluid distribution system (not shown). The flanges would be secured together by conventional bolts 26, 28 with conventional gasket means (not shown) positioned between the respective flanges. A source of microwave energy 30 is connected to the test cell by waveguide 32, which enters the test cell 10 through conventional sealing means 34 and is connected to a first antenna 36 (see FIG. 3) within the test cell. Similarly a detector means 38 is connected to the test cell by waveguide 40 which enters the test cell 10 through conventional sealing means 42 and is connected to a second antenna 44. The first and second antennas 36, 44 are in spaced alignment.

Figure 2:
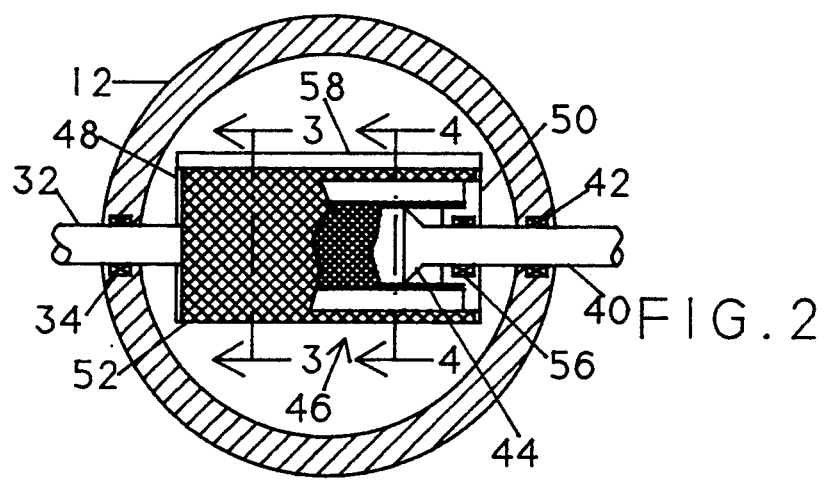
FIG. 2 is a transverse section taken along line 2—2 of FIG. 1, on an enlarged scale and with portions of the subject invention broken away.

As shown in FIGS. 1 and 2, microwave energy from source 30 will pass through waveguide 32 and be radiated by antenna 36 to antenna 44. Antenna 44 receives the microwave energy and passes it through waveguide 40 to the detector 38 in well known fashion.

Cage 46 is a self cleaning device that allows a fluid mixture to flow between antennas 36 and 44 while removing particles and debris that might be in the three phase fluid stream. The cage 46 has two parallel, spaced apart end pieces 48 and 50 designed to support a coarse wire mesh 52 as a cylindrical outside screen and a fine wire mesh 54 as a cylindrical inner screen. The waveguides 32 and 40 pass through bearing means 56 in end plates 48 and 50, so that the cage 46 will rotate about the axis of the waveguides 32 and 40 in response to the flow of the fluid stream through the test cell.

Cage 46 is provided with vanes 58 on the outer surface of the outside screen 52 to assist the cage in rotating, in turbine fashion, as the fluid stream passes through the test cell. Only one vane has been shown, for simplicity of the drawings, and this vane is planar in shape. Clearly profiled vanes could be employed in the present invention.

Figure 4:
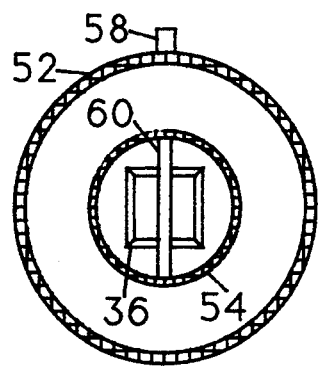
FIGS. 4 to 6 are transverse sections similar to FIG. 3 but taken along line 4—4 and showing three successive steps in the rotation of the cage.
Figure 5:
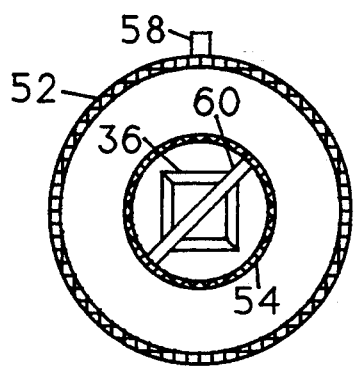
Figure 6:
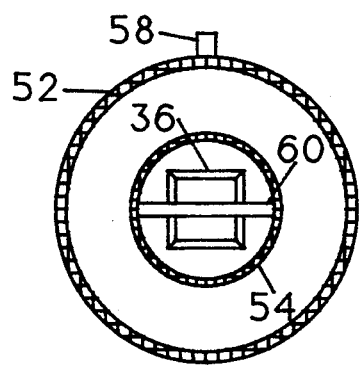
Figure 7:
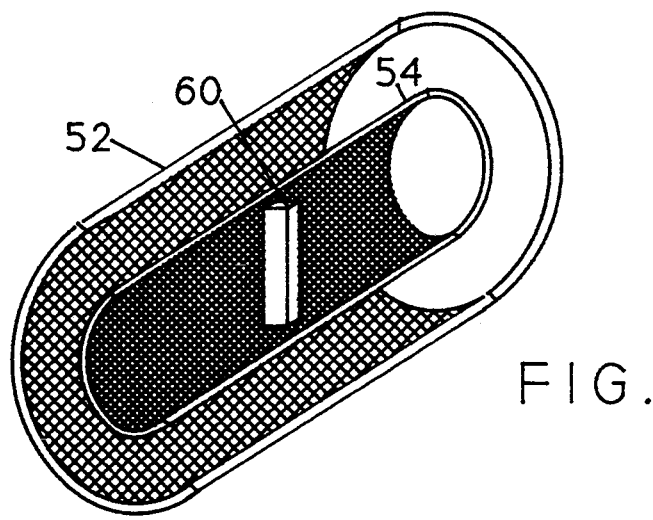
FIG. 7 is a perspective view, partially broken away, of a segment of the cage showing the mounting of the block member.

A rectangular block 60 of some known material, such as Teflon, is mounted within the inner screen 54 perpendicular to and passing through the axis of the bearing means 56, see FIGS. 4 to 6. Rotation of the block 60 about this axis, because of the polarization of the microwave energy passing along the cage axis, causes alteration in the phase shift and attenuation of the passing microwave energy. The frequency and shape of this alteration is directly related to the shape and angular position of the block 60. Referring to FIGS. 4 to 6, and assuming a clockwise rotation, show minimum blockage, intermediate blockage and maximum blockage.

Other blocks (not shown) on different cages (also not shown) along the same microwave path could be shaped differently to give a different signature to their modulation of the transmitted energy. This modulation is easily detected by filters or by autocorrelation methods which are commonly known. The frequency of the modulation is related to the rotation of the cage 46 and thus to the velocity of the local fluid flow. Clearly the density of the local fluid flow mixture would effect the rotational speed of the cage 46.

Another feature of the present invention is the use of the fraction detection of the microwave monitor. Knowing the fraction of the mixture at the cage 46 allows adjusting the calibration of the turbine meter component using the fraction of the actual mixture impacting the cage 46.

In operation, as debris in the fluid stream comes in contact with cage 46, the larger elements of the debris make contact with the coarse wire mesh 52 and fall to the bottom of the test cell 10 to be carried away by the flow of the fluid stream. Smaller elements of the debris may enter cage 46, but they will come in contact with fine wire mesh 54 and be stopped from entering that portion of test cage 46 that lies between antennas 36 and 44. The debris stopped by fine wire mesh 54 may be carried for a short period by the fine wire mesh 54 but should fall away under the influences of gravity, the rotation of cage 54, and the washing action of the flowing fluid stream. The fallen smaller elements will pass out of cage 46, due to the flow of the fluid stream so that there is no build up of debris in the vicinity of the microwave energy path between antennas 36 and 44.

The present invention may be subject to many modifications and changes, which will be apparent to those skilled in the art, without departing from the spirit or essential characteristics thereof. The present embodiment should therefor be considered in all respects as being illustrative and not restrictive of the scope of the invention as defined by the appended claims.

We claim:

1. In a three phase fluid monitor having a microwave energy source and microwave detector means, an improved test cell comprising:

test cell housing means providing fluid flow therethrough;

first antenna means mounted in said test cell and connected to the microwave source means for irradiating the fluid stream flowing through the test cell means with microwave energy;

second antenna means mounted in said test cell in spaced opposition to said first antenna means for receiving microwave energy that has passed through the fluid stream and passing it to said detector means;

cage means spatially arranged defining a cylinder enclosing both antenna means for reducing an amount of debris in a portion of the fluid stream flowing between both antenna means, cage means said mounted for rotation at a rate related to fluid velocity; and microwave modulation means mounted within said cage means whereby rotation of said cage causes interruption of said microwave energy with the frequency and shape of said modulation being related to the velocity of the flowing fluid.

2. In a fluid monitor as described in claim 1 in which the cage means further comprises:

first screen means for preventing the debris of a first predetermined size or greater from entering the cage means; and second screen means for preventing debris of a second predetermined size or greater from passing between the two antennas.

3. In a fluid monitor described in claim 2 in which the second predetermined size is smaller than the first predetermined size and the second screen means is located closer to the antennas than the first screen means.

4. In a fluid monitor as described in claim 2 in which the cage means is cylindrical in shape and the first screen means has a diameter greater than the diameter of the second screen means; and the cage means further comprises two end piece means for holding the first and second screen means in spatial relationship to both antennas.

5. In a fluid monitor as described in claim 2 in which each attaching means includes:

bearing assembly means mounted in a different end piece means so to allow the cage means to rotate in response to the fluid stream flow.

6. In a fluid monitor as described in claim 1 further comprising:

at least one vane means attached to said cage means extending generally radially thereof whereby the flowing fluid will strike the vane assisting in driving the cage into rotation.

7. In a fluid monitor according to claim 1 wherein said microwave modulation means comprises:

a block of material mounted within said cage perpendicular to and intersecting the axis between said antenna.

8. In a fluid monitor according to claim 7 wherein said block is formed of Teflon.

9. In a fluid monitor according to claim 7 wherein said block is rectangular.

* * * * *

UNITED STATES PATENT AND TRADEMARK OFFICE
CERTIFICATE OF CORRECTION

PATENT NO. : 5,386,719
DATED : February 7, 1995
INVENTOR(S) : John David Marrelli
Joseph David Stafford It is certified that error appears in the above-indentified patent and that said Letters Patent is hereby corrected as shown below:

Column 3:

Claim 1, line 6, after "means" insert --said--.

Claim 1, line 7, delete "said".

Signed and Sealed this

Twentieth Day of June, 1995

*Attest:*

BRUCE LEHMAN

*Attesting Officer*     *Commissioner of Patents and Trademarks*